US012195420B2

(12) United States Patent
Cotti Comettini et al.

(10) Patent No.: US 12,195,420 B2
(45) Date of Patent: Jan. 14, 2025

(54) PROCESS FOR THE PRODUCTION OF 1,4-BUTANEDIOL FROM RENEWABLE SOURCES AND POLYESTERS OBTAINED THEREFROM

(71) Applicant: NOVAMONT S.P.A., Novara (IT)

(72) Inventors: Marco Cotti Comettini, Brusnengo (IT); Roberto Vallero, Borgo D'Ale (IT); Catia Bastioli, Novara (IT); Luigi Capuzzi, Novara (IT)

(73) Assignee: NOVAMONT S.P.A., Novara (IT)

( * ) Notice: Subject to any disclaimer, the term of this patent is extended or adjusted under 35 U.S.C. 154(b) by 274 days.

(21) Appl. No.: 17/834,151

(22) Filed: Jun. 7, 2022

(65) Prior Publication Data

US 2022/0298090 A1    Sep. 22, 2022

Related U.S. Application Data

(62) Division of application No. 16/766,498, filed as application No. PCT/EP2018/082668 on Nov. 27, 2018, now Pat. No. 11,377,409.

(30) Foreign Application Priority Data

Nov. 27, 2017   (IT) ................. 102017000135678

(51) Int. Cl.
| | | |
|---|---|---|
| *C07C 31/20* | (2006.01) | |
| *B01D 3/00* | (2006.01) | |
| *B01D 3/14* | (2006.01) | |
| *B01D 15/36* | (2006.01) | |
| *C07C 29/76* | (2006.01) | |
| *C07C 29/80* | (2006.01) | |
| *C08G 18/42* | (2006.01) | |
| *C08G 63/181* | (2006.01) | |
| *C08J 5/18* | (2006.01) | |
| *C08L 67/02* | (2006.01) | |
| *C12P 7/18* | (2006.01) | |

(52) U.S. Cl.
CPC .............. *C07C 29/76* (2013.01); *B01D 3/002* (2013.01); *B01D 3/143* (2013.01); *B01D 15/362* (2013.01); *B01D 15/363* (2013.01); *C07C 29/80* (2013.01); *C07C 31/207* (2013.01); *C08G 18/4211* (2013.01); *C08G 63/181* (2013.01); *C08J 5/18* (2013.01); *C08L 67/02* (2013.01); *C12P 7/18* (2013.01); *C08J 2367/02* (2013.01)

(58) Field of Classification Search
CPC . C07C 31/207; C08G 18/4211; C08G 63/181; C08L 67/02
See application file for complete search history.

(56) References Cited

U.S. PATENT DOCUMENTS

| | | |
|---|---|---|
| 2006/0142536 A1 | 6/2006 | Chen et al. |
| 2014/0275465 A1 | 9/2014 | Garikipati |
| 2018/0186927 A1 | 7/2018 | Shirahama et al. |

FOREIGN PATENT DOCUMENTS

| | | |
|---|---|---|
| CA | 2 226 534 A1 | 7/1998 |
| CN | 105283431 A | 1/2016 |
| JP | 2003321568 A | 11/2003 |
| JP | 2006176783 A | 7/2006 |
| JP | 2007-502325 A | 2/2007 |
| JP | 2008101143 A | 5/2008 |
| JP | 2013028657 A | 2/2013 |
| JP | 2014-520933 A | 8/2014 |
| WO | WO 2004/101479 A2 | 11/2004 |
| WO | WO 2013/012707 A1 | 1/2013 |
| WO | WO 2014/152665 A1 | 9/2014 |
| WO | WO 2014/170759 A2 | 10/2014 |
| WO | 2017038949 A1 | 3/2017 |

OTHER PUBLICATIONS

Office Action dated Jul. 6, 2021 by the Japanese Patent Office in the counterpart Japanese patent application JP 2020-529211 and English translation.
Japanese Office Action issued on Feb. 20, 2024 and English translation for corresponding Japanese Application No. 2023-00299.

*Primary Examiner* — Sikarl A Witherspoon
(74) *Attorney, Agent, or Firm* — POLSINELLI PC

(57) ABSTRACT

The invention relates to a process for the production of 1,4-butanediol comprising the preparation of a fermentation broth comprising 1,4-butanediol from renewable sources and water, separation of a liquid fraction comprising said 1,4-butanediol and water from one or more solid fractions, said liquid fraction comprising 2-pyrrolidone in an amount higher than 80 ppm, one or more passages of the resulting liquid fraction through a bed comprising one or more cation-exchange resins thereby providing an output pH of said liquid fraction from 4 to 2, one or more passages of the resulting liquid fraction through a bed comprising one or more anion-exchange resins thereby providing an output pH of said liquid fraction from 8 to 11, and the distillation of the liquid fraction thereby provided so as to obtain a composition having a concentration of said 1,4-butanediol higher than 99.0% by weight and comprising 2-pyrrolidone in an amount lower than 6 ppm. The resulting composition should exhibit an APHA color value after ageing of less than 30.

6 Claims, No Drawings

PROCESS FOR THE PRODUCTION OF 1,4-BUTANEDIOL FROM RENEWABLE SOURCES AND POLYESTERS OBTAINED THEREFROM

CROSS REFERENCE TO RELATED APPLICATIONS

This application is a divisional application of Ser. No. 16/766,498 filed 27 Nov. 2018, which is a National Phase filing under 35 U.S.C. § 371 of PCT/EP2018/082668 filed on 27 Nov. 2018; which application in turn claims priority to application Ser. No. 102017000135678 filed in Italy on 27 Nov. 2017. The entire contents of each application are hereby incorporated by reference.

DESCRIPTION

The present invention relates to a process for the production of 1,4-butanediol from renewable sources via a fermentation route, the 1,4-butanediol so obtained and a polyester of the diacid-diol type or a polyester-polyol obtained from said 1,4-butanediol.

1,4-butanediol is a widely used monomer for the production of various types of products such as, for example, polyesters of the diacid-diol type or polyester-polyols comprising repeating units deriving from at least one dicarboxylic acid and at least one diol. Polyesters comprising repeating units deriving from a carboxylic acid and a diol are now widely used because of their mechanical and workability properties in all fields for the application of thermoplastic polymer materials such as films, moulded and blow-moulded articles and fibres. It is also required that the polyesters so obtained are biodegradable, in particular in accordance with standard EN 13432.

In the present description the term "renewable sources" means sources which, due to their intrinsic characteristic, are naturally regenerated or are not exhaustible in the time scale of human life and, by extension, whose use does not compromise natural resources for future generations. The use of products of renewable origin also contributes to decreasing $CO_2$ in the atmosphere and decreasing the use of non-renewable resources. A typical example of renewable sources is constituted by vegetable crops.

1,4-butanediol may be prepared by various processes which are commonly known in the state of the art, for example it may be obtained from raw materials of petrochemical origin starting from various precursors such as butadiene, acetylene, maleic anhydride or propylene oxide. Alternatively, 1,4-butanediol may be obtained from renewable sources by means of fermentation processes starting from carbohydrates such as sugars and lignocellulose biomass. For example, WO 2015/158716 describes a process for the production of 1,4-butanediol comprising the fermentation of a culture medium by a microorganism having at least one metabolic pathway for the synthesis of 1,4-butanediol, in which said culture substrate comprises a mixture of glucose and saccharose.

In particular the 1,4-butanediol from renewable sources generally contains various impurities, including by-products directly deriving from the fermentation process, as well as by-products deriving from processes of the degradation of the 1,4-butanediol.

These impurities may have an adverse effect on the polyesters of the diacid-diol type or on the polyester-polyols obtained from the 1,4-butanediol from renewable sources.

For example, high contents of impurities containing nitrogen atoms, generally deriving from the raw materials used in the fermentation process during the synthesis of 1,4-butanediol from renewable sources and, in particular, from amino acids, proteins, ammonium salts, urea and microorganisms deriving from the fermentation process itself give rise to polyesters which are less resistant to hydrolysis.

Furthermore, impurities due to 2-(4'-hydroxybutoxy)-tetrahydrofuran, which is produced by the cyclisation reaction through the dehydration of 1,4-butanediol, if present in high quantities, give rise to solid by-products which are deposited in the reactor during the process of polyester synthesis and limit its productivity.

Also, in the cases of batch polymerization processes the impurities present in 1,4-butanediol from renewable sources may require substantial changes in the process conditions in order to adjust the final viscosity of the desired polyester.

The processes which have currently been developed for the purification of 1,4-butanediol from renewable sources comprise separation systems generally based on distillation columns. The purification systems known in the state of the art may include the addition of agents of various kinds during at least one of the stages in the distillation in order to remove the impurities present.

For example it is known that the addition of reducing agents during at least one of the stages of distillation ensures color stability in the final product.

The presence of 2-(4'-hydroxybutoxy)-tetrahydrofuran can also have an adverse effect on tetrahydrofuran (THF) synthesis. For example, EP 2 730 566 specifically describes a process for the production of THF starting from 1,4-butanediol with a 2-(4'-hydroxybutoxy)-tetrahydrofuran content of up to 3500 ppm.

There is therefore a need to develop a process for the production of 1,4-butanediol from renewable sources which makes it possible to increase its purity so that the 1,4-butanediol so obtained can be advantageously used in the synthesis of biodegradable polyesters of the diacid-diol type or polyester-polyols.

In searching for a new process for the production of 1,4-butanediol from renewable sources the Applicant has now surprisingly found that, during the stage of the purification of an aqueous composition of 1,4-butanediol from renewable sources, the combination of passages, through cationic exchange resin and anionic exchange resin at particular pH ranges makes it possible to drastically reduce the 2-pyrrolidone content of the 1,4-butanediol so obtained.

In a first aspect, therefore, the present invention relates to a process for the production of 1,4-butanediol from renewable sources, said process comprising:

(1) preparation of a fermentation broth comprising 1,4-butanediol from renewable sources and water, and subsequent purification of the same comprising:

(2) separation of a liquid fraction comprising 1,4-butanediol from renewable sources and water from one or more solid fractions, said liquid fraction comprising 2-pyrrolidone in an amount in excess of 80 ppm, (3) one or more passages of the residual liquid fraction through a bed comprising one or more cation exchange resins until a pH from 4 to 2 is obtained when said fraction leaves, (4) one or more passages of the residual liquid fraction through a bed comprising one or more anionic exchange resins until a pH from 8 to 11 is obtained when said liquid fraction leaves, and (5) distillation of the liquid fraction so obtained so as to obtain a 1,4-butanediol composition from renewable sources having a concentration of said 1,4-butanediol higher than 99.0% by weight and comprising 2-pyrrolidone in a quantity of less than 6 ppm.

In the meaning of the present invention the expression "1,4-butanediol from renewable sources" is meant 1,4-butanediol obtained from the process of the fermentation of at least one sugar in the presence of one or more microorganisms having at least one metabolic pathway for synthesis of said 1,4-butanediol.

The process for the production of 1,4-butanediol from renewable sources according to the present invention advantageously does not require post-treatment processes which are generally used in the processes in the state of the art for further purification and, therefore, stabilization of the final product. In fact, the process according to the invention is advantageously carried out in the absence of one or more auxiliary agents such as, for example, reducing agents. Non-limiting examples of reducing agents include sodium borohydride and lithium aluminum hydride.

In a second aspect the present invention relates to a 1,4-butanediol composition from renewable sources having a concentration of said 1,4-butanediol higher than 99.0% by weight and comprising 2-pyrrolidone in a quantity of less than 6 ppm, said composition having an APHA color value of less than 30, preferably less than 15, more preferably less than 10.

The 1,4-butanediol composition from renewable sources according to the invention is advantageously obtained from the process according to the invention.

The composition according to the invention preferably has a concentration of said 1,4-butanediol of between 99.1% and 99.9% by weight, preferably between 99.5% and 99.9% by weight.

It has been found that the composition according to the invention surprisingly maintains stable APHA color values over time. In particular, the composition according to the invention maintains APHA color values which are unchanged during stages of storage, for example at temperatures above 20° C., typically above 50° C.

The composition according to the invention typically has an APHA color value after ageing of less than 30, preferably less than 15, more preferably less than 10.

The APHA color value may be measured using any of the conventionally known methods in the state of the art such as, for example, by photometry. Typically the APHA color value is measured using standard method DIN EN ISO 6271-1.

The composition according to the invention preferably comprises 2-pyrrolidone in a quantity of 5 ppm or less, preferably 4 ppm or less, more preferably 3 ppm or less, and even more preferably 2.5 ppm or less.

If 2-pyrrolidone is present, the composition according to the invention preferably comprises 2-pyrrolidone in a quantity of 0.01 ppm or more, more preferably 0.02 ppm or more.

The 2-pyrrolidone content may be measured by any of the methods conventionally known in the state of the art. Typically 2-pyrrolidone content is measured by combustion of a sample in an inert atmosphere and analysis of the combustion gases by means of analysers for compounds containing nitrogen atoms, generally by means of chemiluminescence analysers. The composition according to the invention may also comprise 2-(4'-hydroxybutoxy)-tetrahydrofuran in a quantity of less than 800 ppm, preferably less than 600 ppm, more preferably 550 ppm or less.

If 2-(4'-hydroxybutoxy)-tetrahydrofuran is present, the composition according to the invention preferably comprises 2-(4'-hydroxybutoxy)-tetrahydrofuran in a quantity of between 50 and 600 ppm, preferably between 100 and 550 ppm.

The 2-(4'-hydroxybutoxy)-tetrahydrofuran content may be measured using any of the methods conventionally known in the start of the art. Typically 2-(4'-hydroxybutoxy)-tetrahydrofuran content is measured using gas chromatography.

The composition according to the invention may also comprise water, typically in a quantity less than 500 ppm, preferably 350 ppm or less.

For the purposes of the present invention the term "ppm" is intended to define a value of a substance expressed in parts per million, that is in milligrams (mg) for every kilogram (kg) of substance.

The composition according to the invention may advantageously be used in a process for the production of a polyester-polyol also as intermediate in the synthesis of polyurethanes when reacted with isocyanates.

The composition according to the invention may advantageously be used in a process for the production of a polyester of the diacid-diol type (described hereinafter as "polyester").

In a third aspect, therefore, the present invention relates to the use of the composition according to the invention in a process for the production of a polyester of the diacid-diol type.

The process for the production of a polyester according to the invention advantageously requires residence times which are shorter than those required by processes carried out in the presence of 1,4-butanediol containing 2-pyrrolidone in a quantity of 6 ppm or more.

In a fourth aspect, the present invention relates to a polyester comprising:
  (a) a dicarboxylic component comprising:
  (a1) 0-80% in moles, with respect to the total dicarboxylic component, of units deriving from at least one aromatic dicarboxylic acid, and
  (a2) 20-100% in moles, with respect to the total dicarboxylic component, of units deriving from at least one aliphatic dicarboxylic acid, and
  (b) a diol component comprising units deriving from a 1,4-butanediol composition from renewable sources having a concentration of said 1,4-butanediol of more than 99.0% by weight and comprising 2-pyrrolidone in a quantity of less than 6 ppm.

In another embodiment, the present invention relates to a polyester comprising:
  (a) a dicarboxylic component comprising:
  (a1) 0-80% in moles, with respect to the total dicarboxylic component, of units deriving from at least one aromatic dicarboxylic acid, and
  (a2) 20-100% in moles, with respect to the total dicarboxylic component, of units deriving from at least one aliphatic dicarboxylic acid, and
  (b) a diol component obtained from the process of production of 1,4-butanediol obtained from renewable sources according to the first aspect of the present invention.

The 1,4-butanediol composition from renewable sources used in the process for the production of a polyester according to the invention is advantageously the composition according to the invention.

The polyester according to the invention is advantageously biodegradable, preferably in accordance with standard EN 13432.

The polyester according to the invention surprisingly has lower color values than a similar polyester in which the diol is substituted by a 1,4-butanediol composition comprising 2-pyrrolidone in a quantity of 6 ppm or more.

In addition to this, the polyester according to the invention has excellent mechanical properties.

In stage (1) of the process according to the invention the fermentation broth is advantageously obtained from a process for the production of 1,4-butanediol from renewable sources via a fermentation route.

The process for the production of 1,4-butanediol from renewable sources via the fermentation route is generally carried out in accordance with one of the processes commonly known in the state of the art, such as for example the process described in WO 2015/158716.

In stage (1) of the process according to the invention a fermentation broth comprising 1,4-butanediol from renewable sources and water is generally prepared through a process comprising fermentation of a culture medium comprising at least one sugar, preferably glucose and, optionally, one or more sugars other than glucose, in the presence of one or more microorganisms having at least one metabolic pathway for the synthesis of 1,4-butanediol.

The culture medium may also comprise other substances which are necessary for the growth and support of the microorganism during the fermentation stage by providing it with elements such as for example C, H, O, N, K, S, P, Fe, Ca, Co, Mn, Mg. Typically, the culture medium may also comprise one or more components selected from the group consisting of sugars other than glucose, protein hydrolysates, proteins, amino acids, organic acids, vitamins, mineral salts, yeast extracts, and microelements such as for example cobalt, calcium and copper. Cobalt, calcium and copper may be added to the culture medium, for example, as salts such as cobalt chloride, calcium chloride and copper chloride. Generally the culture medium comprises at least one sugar, generally glucose, and optionally one or more sugars other than glucose, in a concentration of between 10 and 100 g/L. Because the microorganism consumes one or more sugars during the fermentation stage according to the present process it is generally necessary to top up said sugars in a fermentation reactor. Said topping up may be performed continuously or in batch mode, in a manner known to those skilled in the art.

Also, in order to limit the content of unused sugars and, therefore, to optimize the economic viability of the process, the feed of one or more sugars is advantageously interrupted or gradually diminished before the end of the fermentation. With regard to other possible components of the culture medium, the culture medium generally contains salts, essential minerals and antifoaming agents. The culture medium may be prepared according to any of the means known to those skilled in the art, for example by mixing all its components together or by premixing all the components apart from glucose, and adding the latter subsequently, individually or already premixed. It is also possible to use a commercially available culture medium as a starting base and change its composition subsequently, for example at the time when the culture medium is placed in contact with the microorganism having at least one metabolic pathway for the synthesis of 1,4-butanediol from renewable sources. In the process for the synthesis of 1,4-butanediol from renewable sources, before starting the fermentation or during a stage prior thereto, it is possible to place one or more microorganisms in contact with any suitable culture medium which optionally comprises at least one sugar, in order to encourage growth of the microorganisms. Said stage may be repeated one or more times according to requirements, to ensure a sufficient initial microorganism content. During the fermentation the whole comprising the microorganism and the culture medium comprising one or more sugars is held under suitable conditions to make use of the metabolic pathway for the synthesis of 1,4-butanediol from renewable sources. Those skilled in the art will moreover be able to check the progress of the process during the course of the fermentation, for example by monitoring one or more parameters and if necessary acting upon these in order to return the process to conditions suitable for the production of 1,4-butanediol. With regard to the metabolic pathway for the synthesis of 1,4-butanediol, this may be present in the microorganism in a natural state or may be created artificially, for example by altering, modifying, amplifying, eliminating, or limiting existing metabolic pathways in the microorganism, inserting genetic material therein originating from one or more other organisms, inducing spontaneous genetic mutations, adding chemical compounds which inhibit or stimulate said metabolic pathway during the process, or in any event making use of any genetic engineering technique. Microorganisms having metabolic pathways for the synthesis of 1,4-butanediol and are known to those skilled in the art and are, for example, described in Yim H. et ah, Nature Chemical Biology, Vol. 7, July 2011, p. 445-452 (hereinafter "Yim et al. 2011") and in patent applications WO 2008/115840, WO 2009/023493, WO 2010/030711, WO 2010/071697, WO 2010/141780, WO 2010/141920, WO 2011/031897, WO 2011/047101, WO 2011/066076, WO 2012/177943, AU 2013/3204409, AU 2013/3204038, AU 2013/202623, AU 2013/203176, AU 2013/203177, AU 2013/203342, AU 2013/203440, AU 2013/203480, AU 2013/203163. The fermentation broth in stage (1) of the process according to the invention may also comprise one or more elements including one or more microorganisms, cell residues, possibly unreacted sugars, by-products, metabolites and any components of the culture medium which have not been assimilated or metabolized by said microorganism.

With regard to stage (2) of the process according to the invention, the solid fractions generally contain one or more elements including one or more microorganisms, cell residues, possible unreacted sugars, by-products, mineral salts, metabolites and possible components of the culture medium which have not been assimilated or metabolized by said microorganism.

In the meaning of the present invention, by solid fractions are meant also suspensions and slurries.

In stage (2) of the process according to the invention it is possible to treat the reaction medium originating from the fermentation with one or more treatments selected from settling, centrifuging, filtration, microfiltration, nanofiltration, ultrafiltration, ion exchange, osmosis, other suitable solid/liquid separation techniques and combinations thereof. For example, the reaction medium may be first centrifuged and then filtered, microfiltered, nanofiltered, ultrafiltered and finally subjected to osmosis. In stage (2) of the process according to the invention it is also possible to provide one or more operations for evaporation of the reaction medium or the various intermediate fractions in order to remove some of the water present therein. In stage (2) of the process according to the invention the liquid fraction obtained may also be further purified, for example by treating the liquid fraction comprising 1,4-butanediol from the renewable source and water with one or more treatments selected from evaporation, distillation, rectification or combinations thereof. Said purification may for example be performed using equipment making use of the different volatilities of the components in the liquid phase comprising 1,4-butanediol from renewable sources and water. In one embodiment of the process according to the invention the liquid phase comprising 1,4-butanediol from renewable sources and water is fed to one or more pieces of equipment to separate out at least a vapor phase and at least a condensate by heating and/or condensing at least part of said vapor phase obtaining a final composition essentially comprising 1,4-butanediol from renewable sources.

The liquid fraction obtained in stage (2) of the process according to the invention typically comprises 2-pyrrolidone in a quantity in excess of 100 ppm.

The liquid fraction obtained in stage (2) of the process according to the invention typically comprises 2-(4'-hydroxybutoxy)-tetrahydrofuran in a quantity in excess of 1500 ppm.

The liquid fraction obtained in stage (2) of the process according to the invention generally comprises up to 50% by weight, preferably up to 30% by weight, more preferably up to 20% by weight of water with respect to the total weight of the liquid fraction.

The liquid fraction obtained in stage (2) of the process according to the invention generally comprises 50-95% by weight, preferably 70-90% by weight, more preferably 75-85% by weight of 1,4-butanediol from renewable sources with respect to the total weight of the liquid fraction.

In stage (3) of the process according to the invention the cationic exchange resin is generally selected from the group consisting of resins deriving from strong acids (e.g. sulfonate groups) or weak acids (e.g. carboxylate groups). The cationic exchange resin preferably contains functional groups selected from the group consisting of sulfonate groups. Non-limiting examples of cationic ion exchange resins which are useful in the process according to the invention include, for example, the resin which is commercially available under the trademark DOWEX® 88 or DOWEX® 88 MB.

In stage (3) of the process according to the invention, the pH on leaving is between 4 and 2, preferably between 4 and 3, even more preferably between 3.6 and 3.

In stage (4) of the process according to the invention the anionic exchange resin is generally selected from the group consisting of resins deriving from strong bases (e.g. quaternary amine groups) or weak bases (e.g. tertiary amine groups). The anionic exchange resin preferably contains functional groups selected from the group consisting of quaternary amine groups. Non-limiting example of anionic exchange resins which are useful in the process according to the invention include, for example, the commercially available resin having the trademark DOWEX® 22.

In stage (4) of the process according to the invention, the pH on leaving is between 8 and 11, preferably between 8 and 10, more preferably between 8 and 9.5, ever more preferably between 8.6 and 9.5.

The order of succession of stages (3) and (4) of the process according to the invention is not particularly limiting. Stage (3) may precede or follow stage (4). Preferably stage (3) precedes stage (4).

In stage (5) of the process according to the invention the distillation is generally performed using one or more distillation columns. The distillation preferably comprises at least one stage for the removal of water, at least one stage for the removal of heavy fractions and at least one stage for the removal of light fractions. The distillation may be performed using any of the processes known in the state of the art, for example as described in WO 2014/152665.

According to one embodiment of the invention distillation is performed by means of at least three distillation columns. According to a preferred embodiment of the invention distillation is performed using three distillation columns, in which the purpose of the first distillation column is to separate out the water, the purpose of the second distillation column is to separate out the heavy fractions and the purpose of the third distillation column is to separate out the light fractions.

The process for the production of a polyester according to the invention typically comprises:
 (i) preparation of an oligomer product through an esterification and/or transesterification reaction of a mixture comprising:
  (a) a dicarboxylic component comprising:
  (a1) 0-80% in moles, with respect to the total dicarboxylic component, of units deriving from at least one aromatic dicarboxylic acid and/or an ester, salt or derivative thereof, and (a2) 20-100% in moles, with respect to the total dicarboxylic component, of units deriving from at least one aliphatic dicarboxylic acid and/or an ester, salt or derivative thereof, and
  (b) a diol component comprising units deriving from the 1,4-butanediol composition from renewable sources as defined above,
 (ii) polycondensation of the oligomer product obtained from stage (i), and
 (iii) granulation of the polyester obtained from stage (ii).

The dicarboxylic acid may advantageously be obtained from renewable sources.

The carboxylic acid may be aliphatic or aromatic and is preferably selected from the group consisting of aromatic dicarboxylic acids of the phthalic acid type, heterocyclic aromatic dicarboxylic compounds, saturated aliphatic dicarboxylic acids, unsaturated aliphatic dicarboxylic acids, their esters, salts and mixtures.

The aromatic dicarboxylic acids of the phthalic acid type are preferably phthalic acid or isophthalic acid, more preferably terephthalic acid, their esters, salts and mixtures. The heterocyclic aromatic dicarboxylic compounds are preferably 2,5-furandicarboxylic acid, 2,4-furandicarboxylic acid, 2,3-furandicarboxylic acid, 3,4-furandicarboxylic acid, more preferably 2,5-furandicarboxylic acid, their esters, salts and mixtures thereof.

The saturated aliphatic dicarboxylic acids are preferably selected from C2-C24, preferably C4-C13, more preferably C4-C11 saturated dicarboxylic acids, their C1-C24, preferably C1-C4 alkyl esters, their salts and mixtures. Preferably the saturated aliphatic dicarboxylic acids are selected from succinic acid, 2-ethylsuccinic acid, glutaric acid, 2-methylglutaric acid, adipic acid, pimelic acid, suberic acid, azelaic acid, sebacic acid, undecandioic acid, dodecandioic acid, brassylic acid and their C1-C24 alkyl esters.

The unsaturated aliphatic dicarboxylic acids are preferably selected from itaconic acid, fumaric acid, 4-methylenepimelic acid, 3,4-bis(methylene)nonandioic acid, 5-methylene-nonandioic acid, their $C_i$-$C_{24}$, preferably $C_1$-$C_4$ alkyl esters, their salts and mixtures thereof. The diol component may also comprise one or more diols other than 1,4-butanediol. Preferably the diol component essentially consists of the 1,4-butanediol composition from renewable sources according to the invention.

If present, the additional diol may be obtained from a fossil source or a renewable source.

If present, the additional diol is typically selected from the group consisting of saturated aliphatic diols and unsaturated aliphatic diols, aromatic diols and mixtures thereof.

More preferably, the saturated aliphatic diols are selected from the group consisting of 1,2-ethanediol, 1,2-propanediol, 1,3-propanediol, 1,5-pentanediol, 1,6-hexanediol, 1,7-heptanediol, 1,8-octanediol, 1,9-nonanediol, 1,10-decanediol, 1,11-undecanediol, 1,12-dodecanediol, 1,13-tridecanediol, 1,4-cyclohexanedimethanol, neopentylglycol, 2-methyl-1,3-propanediol, dianhydrosorbitol, dianhydromannitol, dianhydroiditol, cyclohexanediol, cyclohexanemethanediol, dialkylene glycols and polyalkylene glycols having a molecular weight of 100-4000, such as for example polyethylene glycol, polypropylene glycol and mixtures thereof.

The unsaturated aliphatic diols are more preferably selected from the group consisting of cis 2-butene-1,4-diol, trans 2-butene-1,4-diol, 2-butyne-1,4-diol, cis 2-pentene-1, 5-diol, trans 2-pentene-1,5-diol, 2-pentyne-1,5-diol, cis 2-hexene-1,6-diol, trans 2-hexene-1,6-diol, 2-hexyne-1,6-diol, cis 3-hexene-1,6-diol, trans 3-hexene-1,6-diol, 3-hexyne-1,6-diol and their mixtures.

The aromatic diols are instead more preferably selected from the group consisting of 2,5-furandimethanol, 2,4-furandimethanol, 2,3-furandimethanol, 3,4-furandimethanol, more preferably 2,5-furandimethanol and mixtures thereof.

In one embodiment of the present invention the repeating polyester units are repeating 1,4-butylene dicarboxylate units deriving from condensation of the composition of 1,4-butanediol from renewable sources according to the invention with mixtures comprising two or more dicarboxylic acids, preferably of the type listed above.

In one preferred embodiment said repeating units derive from mixtures of aromatic dicarboxylic acids and aliphatic dicarboxylic acids comprising, with respect to the total dicarboxylic acids content:
  35-100% in moles, preferably 40-95% in moles, of one or more aromatic dicarboxylic acids or heterocyclic aromatic dicarboxylic compounds, their esters or salts;
  0-65% in moles, preferably 5-60% in moles, of one or more aliphatic dicarboxylic acids, their esters and salts.

In another preferred embodiment said repeating units derive from mixtures comprising at least two aromatic dicarboxylic acids in turn comprising with respect to the total aromatic dicarboxylic acids content:
  1-99% in moles, preferably 5-95% in moles, more preferably 10-80% in moles, of terephthalic acid, its esters or salts;
  99-1% in moles, preferably 95-5% in moles, more preferably 90-20% in moles of 2,5-furandicarboxylic acid, its esters or salts.

In another preferred embodiment of the present invention, said repeating units derive from mixtures comprising at least two saturated aliphatic dicarboxylic acids in turn comprising, with respect to the total aliphatic dicarboxylic acids content, at least 50% in moles, preferably more than 60% in moles, more preferably more than 65% in moles, of one or more saturated aliphatic dicarboxylic acids selected from the group consisting of succinic acid, adipic acid, azelaic acid, sebacic acid, brassylic acid, their $C_i$-$C_{24}$, preferably $C_i$-$C_4$, esters and mixtures thereof.

In the case of copolyesters, these preferably contain 70% in moles, more preferably 80% in moles, of 1,4-butylene dicarboxylate units. In addition to the 1,4-butylene dicarboxylate units said copolyesters preferably comprise alkylene dicarboxylate units in which the alkylene group derives from the condensation of one or more diols which are not 1,4-butanediol, preferably selected from the group consisting of saturated aliphatic diols and unsaturated aliphatic diols, aromatic diols and mixtures thereof.

Examples of typical polyesters are: poly(1,4-butylene succinate), poly(1,4-butylene adipate), poly (1,4-butylene azelate), poly(1,4-butylene sebacate), poly(1,4-butylene adipate-co-1,4-butylene succinate), poly(1,4-butylene azelate-co-1,4-butylene succinate), poly(1,4-butylene sebacate-co-1,4-butylene succinate), poly(1,4-butylene succinate-co-1,4-butylene adipate-co-1,4-butylene azelate), poly(1,4-butylene adipate-co-1,4-butylene azelate), poly(1,4-butylene sebacate-co-1,4-butylene adipate), poly(1,4-butylene-hexadecanedioate), poly(1,4-butylene-octadecanedioate), poly(1,4-butylene-hexadecanedioate-co-1,4-butylene-terephthalate), poly(1,4-butylene-octadecanedioate-co-1,4-butylene terephthalate), poly(1,4-butylene adipate-co-1,4-butylene terephthalate), poly(1,4-butylene sebacate-co-1,4-butylene terephthalate), poly(1,4-butylene azelate-co-1,4-butylene terephthalate), poly(1,4-butylene brassylate-co-1,4-butylene terephthalate), poly(1,4-butylene succinate-co-1,4-butylene terephthalate), poly(1,4-butylene adipate-co-1,4-butylene sebacate-co-1,4-butylene terephthalate), poly(1,4-butylene azelate-co-1,4-butylene sebacate-co-1,4-butylene terephthalate), poly(1,4-butylene adipate-co-1,4-butylene azelate-co-1,4-butylene terephthalate), poly(1,4-butylene succinate-co-1,4-butylene sebacate-co-1,4-butylene terephthalate), poly(1,4-butylene adipate-co-1,4-butylene succinate-co-1,4-butylene terephthalate), poly(1,4-butylene azelate-co-1,4-butylene succinate-co-1,4-butylene terephthalate), poly(1,4-butylene adipate-co-1,4-butylene-2,5-furandicarboxylate), poly(1,4-butylene sebacate-co-1,4-butylene-2,5-furandicarboxylate), poly(1,4-butylene azelate-co-1,4-butylene-2,5-furandicarboxylate), poly(1,4-butylene brassylate-co-1,4-butylene-2,5-furandicarboxylate), poly(1,4-butylene succinate-co-1,4-butylene-2,5-furandicarboxylate), poly(1,4-butylene adipate-co-1,4-butylene sebacate-co-1,4-butylene-2,5-furandicarboxylate), poly(1,4-butylene azelate-co-1,4-butylene sebacate-co-1,4-butylene-2,5-furandicarboxylate), poly (1,4-butylene adipate-co-1,4-butylene azelate-co-1,4-butylene-2,5-furandicarboxylate), poly(1,4-butylene succinate-co-1,4-butylene sebacate-co-1,4-butylene-2,5-furandicarboxylate), poly(1,4-butylene adipate-co-1,4-butylene succinate-co-1,4-butylene-2.5-furandicarboxylate), poly(1,4-butylene azelate-co-1,4-butylene succinate-co-1,4-butylene-2.5-furan-dicarboxylate), poly(1,4-butylene-hexadecanedioate-co-1,4-butylene-2,5-furandicarboxylate), poly (1,4-butylene-octadecanedioate-co-1,4-butylene-2,5-furandicarboxylate)

The polyesters according to the present invention preferably comprise, in addition to the 1,4-butylene dicarboxylate unit and any different alkylene dicarboxylate units, repeating units deriving from at least one hydroxy acid in a quantity of between 0 and 49% in moles, preferably between 0 and 30% in moles, with respect to the total moles of dicarboxylic component.

Examples of convenient hydroxy acids are glycolic acid, hydroxybutyric acid, hydroxycaproic acid, hydroxyvaleric acid, 7-hydroxyheptanoic acid, 8-hydroxycaproic acid, 9-hydroxynonanoic acid, lactic acid or lactides. The hydroxy acids may be inserted into the chain as such or may also be first caused to react with dicarboxylic acids or diols.

The polyester of diacid-diol type according to the present invention has an MFR (measured in accordance with standard ISO 1133-1 at 190° C. and 2.16 kg) within the range 1-50 g/10 min, preferably 1.5-30 g/10 min, more preferably 2-20 g/10 min, even more preferably 3-10 g/10 min.

In a fifth aspect the present invention relates to a mixture comprising:
- at least one polyester according to the invention, and
- one or more polyesters other than said polyester.

The mixture according to the present invention preferably comprises:
- at least one polyester according to the invention, and
- 1-70% by weight, with respect to the weight of the polyester, of one or more polymers other than said polyester.

The mixture according to the present invention is typically produced by mixing, preferably in an extruder, at a temperature of between 150° C. and 250° C., with one or more polymers, typically in quantities of 1-70% by weight with respect to the weight of the polyester. Said polymers are generally selected from the group consisting of hydroxy acid polyesters, polyolefins, aromatic polyesters not including 1,4-butylene dicarboxylate units, polyester- and polyether-urethanes, polyurethanes, polyamides, poly amino acids, polyethers, polyureas, polycarbonates and/or one or more additives selected from fillers, plasticisers, UV stabilisers, lubricants, nucleating agents, surfactants, antistatic agents, pigments, flame-retardant agents, compatibilising agents, polyphenols, reinforcing fillers, coupling agents, antioxidants, anti mould agents, waxes and process coadjuvants.

Among the hydroxy acid polyesters, the following are preferred: polyesters of lactic acid, poly-8-caprolactone, polyhydroxybutyrate, polyhydroxybutyrate-valerate, polyhydroxybutyrate-propanoate, polyhydroxybutyrate-hexanoate, polyhydroxybutyrate-decanoate, polyhydroxy-butyrate-dodecanoate, polyhydroxybutyrate-hexadecanoate, polyhydroxybutyrate-octadecanoate, poly 3-hydroxybutyrate-4-hydroxybutyrate.

Preferably the hydroxy acid polyesters comprise at least 80% by weight, with respect to the total weight of hydroxy acid polyesters, of one or more polyesters of lactic acid. The polyesters of lactic acid are preferably selected from the group consisting of poly L-lactic acid, poly D-lactic acid, poly D, L-lactic acid stereocomplex, copolymers comprising more than 50% in moles of said polyesters of lactic acid or mixtures thereof. Particularly preferred are polyesters of lactic acid containing at least 95% by weight of repeating units deriving from L-lactic or D-lactic acid or combinations thereof, typically having a weight average molecular weight (Mw) of over 50,000 and a dynamic viscosity of between 50 and 700 Pas, preferably between 80 and 500 Pas (measured according to standard ASTM D3835 at T of 190° C., velocity gradient of 1000 s$^1$, D of 1 mm, and L/D of 10), such as for example the products having the trademarks Ingeo™ Biopolymer 4043D, 3251D and 6202D.

Preferably a mixture comprising at least one polyester according to the present invention and at least one hydroxy acid polyester comprises between 1% and 80% by weight, preferably between 2% and 70% by weight of said hydroxy acid polyesters with respect to the sum of the weights respectively of the polyesters obtained from the process according to the present invention and the latter.

Among the polyolefins, the following are preferred: polyethylene, polypropylene, their copolymers, polyvinyl alcohol, polyvinyl acetate, poly ethyl-vinyl acetate and polyethylene vinyl alcohol.

Among the aromatic polyesters, the following are preferred: PET, PBT, PTT in particular having a renewable content of more than 30% and polyalkylene furandicarboxylates. Among the latter particularly preferred are poly(1,2-ethylene-2,5-furandicarboxylate), poly(1,3-propylene-2,5-furandicarboxylate), poly(1,4-butylene-2,5-furandicarboxylate) and their mixtures.

Examples of polyamides are as follows: polyamide 6 and 6.6, polyamide 9 and 9.9, polyamide 10 and 10.10, polyamide 11 and 11.11, polyamide 12 and 12.12 and combinations thereof of the 6/9, 6/10, 6/11 or 6/12 type.

The polycarbonates may be selected from the group consisting of polyethylene carbonates, polypropylene carbonates, polybutylene carbonates, their mixtures and copolymers.

The polyesters may be selected from the group consisting of polyethylene glycols, polypropylene glycols, polybutylene glycols, their copolymers and their mixtures having molecular weights from 70,000 to 500,000.

Preferably a mixture comprising at least one polyester according to the present invention and at least one polymer selected from the group consisting of polyolefins, aromatic polyesters, polyester- and polyether-urethanes, polyurethanes, polyamides, poly amino acids, polyethers, polyureas, polycarbonates and their mixtures comprise between 5% and 80% by weight, more preferably between 10% and 60% by weight of said polymers, with respect to the sum of the weights respectively of the polyesters obtained by the process according to the present invention and said polymers.

Fillers are preferably selected from the group consisting of kaolin, barytes, clay, talc, carbonates or calcium and magnesium, iron and lead, aluminium hydroxide, diatomaceous earth, aluminium sulfate, barium sulfate, silica, mica, titanium dioxide, wollastonite, starch, cellulose, chitin, chitosan, alginates, proteins such as gluten, zein, casein, collagen, gelatin, natural gums, rosinic acid and derivatives and mixtures thereof.

By the term starch is meant all types of starch, in particular the following: flour, native starch, hydrolysed starch, destructured starch, gelatinised starch, plasticised starch, thermoplastic starch, biofiller comprising complexed starch or mixtures thereof. Particularly suitable according to the invention are starches such as those form potato, maize, tapioca and peas.

Starches which are capable of being easily destructured and which have high initial molecular weights, such as for example potato starch and maize starch, have proved to be particularly advantageous. Starch and cellulose may be present either as such or in chemically modified form, such as for example in the form of starch or cellulose esters having a degree of substitution of between 0.2 and 2.5, starch hydroxypropylate, starch modified with fatty chains, or as cellophan.

In the case of destructured starch reference is made here to the teaching included in patents EP 0 118 240 and EP 0 327 505, by such being meant starch processed in such a way as not to show substantially the so-called "Maltese crosses" under the optical microscope in polarized light and the so-called "ghosts" under an optical microscope in phase contrast.

Advantageously destructuring of the starch is brought about through a process of extrusion at a temperature of between 110° C. and 250° C., preferably between 130° C.

and 180° C., preferably at pressures of between 0.1 MPa and 7 MPa, preferably between 0.3 MPa and 6 MPa, preferably providing a specific energy of more than 0.1 kWh/kg during said extrusion. Said destructuring may be performed either during stage (2) of the process according to the invention or in a separate phase, then feeding the starch in already destructured form, to stage (2) of the process.

Destructuring of the starch preferably takes place in the presence of 1-40% by weight, with respect to the weight of the starch, of one or more plasticisers selected from water and polyols having from 2 to 22 carbon atoms. With regard to the water, this may also be that which is naturally present in the starch. Among the polyols, polyols having from 1 to 20 hydroxyl groups containing from 2 to 6 carbon atoms, their ethers, thioethers and organic and inorganic esters are preferred. Examples of polyols are glycerine, diglycerol, polyglycerol, pentaerythritol, polyglycerol ethoxylate, ethylene glycol, polyethylene glycol, 1,2-propanediol, 1,3-propanediol, 1,4-butanediol, neopentylglycol, sorbitol monoacetate, sorbitol diacetate, sorbitol monoethoxylate, sorbitol diethoxylate, and mixtures thereof. In a preferred embodiment the starch is destructured in the presence of glycerol or a mixture of plasticisers comprising glycerol, more preferably comprising 2-90% by weight of glycerol. Preferably the destructured starch comprises 1-40% by weight with respect to the weight of the starch of plasticisers selected from those listed above. Compositions comprising destructured starch are particularly preferred. Preferably the starch in the mixture is present in the form of particles having a circular or elliptical cross-section or a cross-section which is in any event similar to an ellipse having a mean arithmetic diameter of less than 1 pm and more preferably less than 0.5 pm median diameter measured with reference to the major axis of the particle. With regard to the cellulose, this may for example be present in the form of cellulose fibres or as wood flour.

Advantageously more than one filler may be used in the mixture according to the present invention. Particularly preferred are mixtures containing starch and at least one other filler. With regard to the plasticisers, one or more plasticisers selected from the group consisting of phthalates, such as for example diisononyl phthalate, trimellitates, such as for example esters of trimellitic acid with $C_4$-$C_{20}$ monoalcohols preferably selected from the group consisting of n-octanol and n-decanol, and aliphatic esters having the structure below may be present in addition to any plasticisers preferably used for preparation of the destructured starch described above:

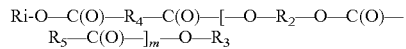

in which

Ri is selected from one or more of the groups comprising H, saturated and unsaturated linear and branched alcohol residues of the $C_i$-$C_{24}$ type, polyol residues esterified with $C_i$-$C_{24}$ monocarboxylic acids;

$R_2$ comprises —$CH_2$—$C(CH_3)_2$—$CH_2$— groups and $C_2$-$C_g$ alkylenes, and comprises at least 50% in moles of said —$CH_2$—$C(CH)_2$—$CH_2$— groups;

$R_3$ is selected from one or more of the groups comprising H, saturated and unsaturated linear and branched alkyl residues of the $C_1$-$C_{24}$ type, polyol residues esterified with $C_1$-$C_{24}$ monocarboxylic acids;

$R_4$ and $R_5$, which are the same or different, comprise one or more $C_2$-$C_{22}$, preferably $C_2$-$C_n$, more preferably $C_4$-$C_9$, alkylenes, and comprise at least 50% in moles of $C_7$ alkylenes; and m is an integer of between 1 and 20, preferably between 2 and 10, more preferably between 3 and 7. Preferably, in said esters at least one of the Ri and/or R groups comprises, preferably in a quantity of 10% in moles or more, more preferably 20% in moles or more, even more preferably 25% in moles or more with respect to the total quantity of Ri and/or $R_3$ groups, polyol residues esterified with at least one $C_i$-$C_{24}$ monocarboxylic acid selected from the group consisting of stearic acid, palmitic acid, 9-ketostearic acid, 10-ketostearic acid and mixtures thereof.

Examples of aliphatic esters of this type are described in Italian patent application MI2014A000030 and in applications PCT/EP2015/050336, PCT/EP2015/050338.

When present the selected plasticisers are preferably present in a quantity of between 0.2% and 20% by weight, more preferably between 0.5% and 10% by weight, with respect to the total weight of the mixture. The lubricants are preferably selected from the esters and metal salts of fatty acids such as for example zinc stearate, calcium stearate, aluminium stearate and acetyl stearate.

Preferably, when used, said lubricants are used in a quantity of up to 1% by weight, more preferably up to 0.5% by weight, with respect to the total weight of the mixture. Examples of nucleating agents include the sodium salt of saccharine, calcium silicate, sodium benzoate, calcium titanate, boron nitride, talc, zinc stearate, low molecular weight PLA. These additives are preferably added in quantities up to 10% by weight and more preferably between 2% and 6% by weight with respect to the total weight of polyester. Pigments may also be added if necessary, for example clays, copper phthalocyanine, titanium dioxide, silicates, iron oxides and hydroxides, carbon black and magnesium oxide. These additives are preferably added up to 10% by weight.

With regard to the polyphenols, these are preferably selected from the group consisting of lignin, silybin, silydianin, isosilybin and silychristin and mixtures thereof, and are present in quantities preferably of between 0.5% and 7% by weight with respect to the total weight of the mixture.

In a preferred embodiment the polyphenol of plant origin advantageously comprises a mixture comprising silybin, silydianin, isosilybin and silychristin. Said mixture may advantageously be obtained by alcoholic extraction from the de-oiled cake of seeds of the milk thistle (*Silybum marianum*) and is commonly also known commercially by the name of silymarin. The polyesters obtained from the process according to the present invention are extremely suitable for use, alone or mixed with other polymers, in many practical applications for the manufacture of products such as for example films, fibres, non-woven fabrics, sheets, folded, thermoformed, blow-moulded and expanded articles and articles also laminated using the extrusion coating technique.

In a sixth aspect the present invention relates to a product comprising at least one polyester according to the invention.

In one embodiment of the present invention the product according to the invention comprises the mixture according to the invention.

The product according to the present invention is particularly suitable for use in various applications including food applications.

Examples of products comprising at least one polyester according to the present invention are the following:
  film;
  sacks and bags for organic collection such as the collection of food waste and grass cuttings;
  thermoformed or single layer or multilayer food packaging such as, for example, containers for milk, yoghurt, meat and beverages;

coatings obtained using the extrusion coating technique; multilayer laminates with layers of paper, plastics materials, aluminium, metallised films;

expanded or expandable granules for the production of parts formed by sintering;

expanded and semi-expanded products including expanded blocks formed of pre-expanded particles;

expanded sheets, thermoformed expanded sheets, containers obtained therefrom for food packaging;

containers in general for fruit and vegetables;

compositions with gelatinised, destructured and/or complex starch, natural starch, flours, other fillers of natural, plant or inorganic origin as filler; and fibres, microfibres, composite fibres with a core comprising rigid polymers such as PLA, PET, PTT, etc., and an outer shell of the material according to the invention, dablens composite fibre, fibres having various cross-sections from round to multilobate, flock fibres, woven and non-woven or spun-bonded or thermo-bonded fabrics for the sanitary sector, hygiene, agriculture and clothing. They may also be used in applications as a replacement for plasticised PVC.

The product according to the present invention is preferably a film.

The film according to the present invention may be a mono- or bi-orientated film.

In one embodiment of the present invention the film according to the invention is a multilayer film with other polymer materials.

The film according to the present invention is particularly suitable for use in the agricultural sector as a mulching film.

In addition to this, the film according to the present invention is particularly suitable as a stretch film for foodstuffs, for bales in agriculture and for wrapping wastes.

The following examples illustrate the present invention in a non-limiting way.

Methods of Measurement

The 2-pyrrolidone content (referred to below as "2-P") was determined using combustion of a sample in an inert atmosphere and analysis of the combustion gas using chemiluminescence analysers (Analytik Jena Multi EA5000 analyser).

The content of 2-(4'-hydroxybutoxy)-tetrahydrofuran (referred to below as "HB-THF") was determined by gas chromatography on the product obtained after the distillation stage.

Water content was determined by conventional methods on the product obtained after the distillation stage.

The APHA color value, measured in Pt—Co units, was determined by spectrophotometry in accordance with standard method DIN EN ISO 6271-1 before and after the accelerated ageing test.

The accelerated ageing test was carried out by heating a sample of 1,4-butanediol to 200° C. in a system which was stirred and held under those conditions for two hours. The system was subsequently cooled to room temperature. At the end of the test the thermal stability of the 1,4-butanediol was evaluated by spectrophotometric measurement of the APHA color in accordance with standard method DIN EN ISO 6271-1.

The results are reported in Table 1.

EXAMPLE 1

A 1,4-butanediol composition from renewable sources according to the present invention was obtained from the fermentation broth described in patent application WO 2015/158716.

The fermentation broth so obtained was processed so as to separate out a liquid fraction comprising 1,4-butanediol from renewable sources and water from one or more solid fractions. The liquid fraction so obtained then underwent a purification process through successive microfiltration, nanofiltration, ion exchange and evaporation treatments so as to obtain a liquid fraction containing 20% by weight of water with respect to the total weight of the liquid fraction.

The residual liquid fraction then successively underwent:
(a) a purification process through a bed comprising a cationic exchange resin containing sulfonate groups until a pH of not more than 4 was obtained for said liquid fraction on leaving and subsequently through an ion exchange resin containing quaternary amine groups until a pH of not less than 8 was obtained for the liquid fraction on leaving, and
(b) distillation.

The 2-pyrrolidone and 2-(4'-hydroxybutoxy)-tetrahydrofuran content in the composition so obtained was measured after distillation.

The results are shown in Table 1.

COMPARATIVE EXAMPLE 1

A 1,4-butanediol composition from renewable sources was obtained in accordance with the procedure described in Example 1 except that in stage (a) of said Example 1 the cation exchange resin was used for a longer time than that required to achieve a pH of 4.5 for the liquid fraction on leaving and the anionic exchange resin was kept in operation for a longer time until a pH of 7 was reached for the liquid fraction on leaving.

The 2-pyrrolidone and 2-(4'-hydroxybutoxy)-tetrahydrofuran content in the composition so obtained was measured after distillation.

The results are shown in Table 1.

COMPARATIVE EXAMPLE 2

Commercial grade 1,4-butanediol from a fossil source produced by Markor Chemical Industry Co., Ltd.

As shown by the data provided in Table 1, the composition of the 1,4-butanediol from renewable sources obtained by the process according to the invention such as, for example, the composition described in Example 1 according to the invention unexpectedly has lower 2-pyrrolidone values than the 2-pyrrolidone values for the materials obtained according to each of Comparative Examples 1 and 2.

Furthermore, as shown by the data provided in Table 2, the composition of the 1,4-butanediol from renewable sources obtained by the process according to the invention such as, for example, the composition described in Example 1 according to the invention, advantageously has a stable APHA color value over time, without requiring any post-treatment procedures for further purification and, therefore, the stabilization of the final product that is typically necessary in the case of 1,4-butanediol from fossil sources. In particular, as shown by the data provided in Table 1, the composition of the 1,4-butanediol from renewable sources obtained by the process according to the invention surprisingly maintains APHA color values of less than 10 before and after the accelerated ageing test.

TABLE 1

|  | Example 1 | Example C. 1 | Example C. 2 |
|---|---|---|---|
| 1,4-butanediol [% by weight] | 99.9 | 99.8 | 99.6 |

TABLE 1-continued

|  | Example 1 | Example C. 1 | Example C. 2 |
|---|---|---|---|
| 2-P [ppm] | 2.5 | 6.9 | 142 |
| HB-THF [ppm] | 530 | 201 | 684 |
| Water [ppm] | 350 | 16 | 152 |
| APHA color | 5 | 16 | 5 |
| APHA color (after the accelerated ageing test) | <10 | 33 | N.A. |

PREPARATION OF POLYESTERS OF EXAMPLES 2 AND 3

The reagents terephthalic acid, adipic acid and/or azelaic acid, 1,4-butanediol (according to Example 1) and the esterification catalyst (Tyzor TE®) were loaded into a 25 geometrical litre steel reactor provided with oil heating, a distillation column, a vacuum line with a distillates knockdown system and mechanical stirring.

The reactor was sealed in nitrogen and the stirrer was switched on and the temperature was gradually raised to 220° C. over a time of 1 hour during which the water deriving from the esterification process began to distil off. The temperature was then raised to 240° C. for approximately a further hour.

Distillation was allowed to proceed for 1 hour at 240° C., at the end of which the apparent conversion was 100% or more.

At the end of the esterification stage polymerisation catalyst (1000 ppm of tetraorthobutyl titanate, TnBt) was added, the temperature of the melt was held at 240° C. and the pressure was gradually reduced to below 2 mbar over a time of approximately 30 minutes.

The reaction was continued for 4 hours holding the temperature of the melt at 240° C. until the desired inherent viscosity was achieved.

The material was then discharged as filaments through a spinner, cooled in a water bath and granulated into pellets.

EXAMPLE 2

A polyester poly(1,4-butylene adipate-co-1,4-butylene azelate-co-1,4-butylene terephthalate) with 48% mol of 1,4-butylene terephthalate units, with 16% mol of azelaic acid units, and with 36% mol of adipic acid units with respect to the total dicarboxylic component, was obtained. The 1,4-butylene units of said polyester were obtained by 1,4-butanediol according to Example 1.

EXAMPLE 3

A polyester poly(1,4-butylene adipate-co-1,4-butylene terephthalate) with 47% mol of 1,4-butylene terephthalate units, and with 53% mol of adipic acid units with respect to the total dicarboxylic component, was obtained. The 1,4-butylene units of said polyester were obtained by 1,4-butanediol according to Example 1.

The MFR values of polyesters according to Examples 2 and 3 are reported in Table 2.

TABLE 2

| Example | Composition of 1,4-butylene units | MFR [g/10 min at 190° C., 2.16 kg] |
|---|---|---|
| 2 | Example 1 | 6.2 |
| 3 | Example 1 | 5.1 |

What is claimed is:

1. A polyester comprising repeating 1,4-butylene dicarboxylate units deriving from condensation of a composition of 1,4-butanediol from renewable sources with mixtures comprising two or more dicarboxylic acids,
   wherein the composition has a concentration of 1,4-butanediol higher than 99.0% by weight and comprises 2-pyrrolidone in an amount lower than 6 ppm and 2-(4'-hydroxybutoxy)-tetrahydrofuran in an amount lower than 800 ppm and has an APHA color value after ageing of less than 30.

2. The polyester according to claim 1, wherein the repeating units derive from mixtures of aromatic dicarboxylic acids and aliphatic dicarboxylic acids comprising, with respect to the total dicarboxylic acids content:
   35-100% in moles of one or more aromatic dicarboxylic acids or heterocyclic aromatic dicarboxylic compounds, their esters or salts thereof;
   0-65% in moles of one or more aliphatic dicarboxylic acids, their esters or salts thereof.

3. The polyester according to claim 2, wherein the repeating units derive from mixtures of aromatic dicarboxylic acids and aliphatic dicarboxylic acids comprising, with respect to the total dicarboxylic acids content:
   40-95%, in moles of one or more aromatic dicarboxylic acids or heterocyclic aromatic dicarboxylic compounds, their esters or salts thereof;
   5-60%, in moles of one or more aliphatic dicarboxylic acids, their esters or salts thereof.

4. The polyester according to claim 1, wherein the repeating units derive from mixtures comprising at least two aromatic dicarboxylic acids in turn comprising with respect to the total aromatic dicarboxylic acids content:
   1-99% in moles of terephthalic acid, its esters or salts thereof,
   99-1% in moles of 2,5-furandicarboxylic acid, its esters or salts thereof.

5. The polyester according to claim 1, wherein the repeating units derive from mixtures comprising at least two saturated aliphatic dicarboxylic acids in turn comprising, with respect to the total aliphatic dicarboxylic acids content, at least 50% in moles of one or more saturated aliphatic dicarboxylic acids selected from the group consisting of succinic acid, adipic acid, azelaic acid, sebacic acid, brassylic acid, their C1-C24 esters and mixtures thereof.

6. The polyester according to claim 5, wherein the esters are C1-C4 esters.

* * * * *